(12) United States Patent
Matthison-Hansen et al.

(10) Patent No.: US 11,553,113 B2
(45) Date of Patent: Jan. 10, 2023

(54) ENDOSCOPE

(71) Applicant: AMBU A/S, Ballerup (DK)

(72) Inventors: Kaspar Mat Matthison-Hansen, Helsingør (DK); Thomas Bachgaard Jensen, Copenhagen (DK); Jakob Bønnelykke Kristensen, Ølstykke (DK)

(73) Assignee: AMBU A/S, Ballerap (DK)

( * ) Notice: Subject to any disclaimer, the term of this patent is extended or adjusted under 35 U.S.C. 154(b) by 120 days.

(21) Appl. No.: 17/204,119

(22) Filed: Mar. 17, 2021

(65) Prior Publication Data

US 2021/0203813 A1  Jul. 1, 2021

Related U.S. Application Data

(63) Continuation of application No. 16/860,831, filed on Apr. 28, 2020, now Pat. No. 10,965,844, which is a
(Continued)

(30) Foreign Application Priority Data

May 27, 2015 (DK) .................................. 201570319

(51) Int. Cl.
*A61B 1/00* (2006.01)
*H04N 5/225* (2006.01)
(Continued)

(52) U.S. Cl.
CPC ......... *H04N 5/2251* (2013.01); *A61B 1/0011* (2013.01); *A61B 1/00066* (2013.01);
(Continued)

(58) Field of Classification Search
None
See application file for complete search history.

(56) References Cited

U.S. PATENT DOCUMENTS

| 609,370 A | 8/1898 | Sargeant |
|---|---|---|
| 609,570 A | 8/1898 | Bowden |

(Continued)

FOREIGN PATENT DOCUMENTS

| AU | 2008207558 A1 | 4/2009 |
|---|---|---|
| CN | 1125390 A | 6/1996 |

(Continued)

OTHER PUBLICATIONS

Article 94(3) EPC communication in related EP appl. No. 16726781. 4, dated Oct. 26, 2018; 5 pgs.
(Continued)

*Primary Examiner* — Timothy J Neal
(74) *Attorney, Agent, or Firm* — Faegre Drinker Biddle & Reath LLP

(57) ABSTRACT

A video endoscope including an operating handle; an insertion tube extending distally from the operating handle; a camera at the distal end of the insertion tube; a working channel extending from the housing to the distal end of the insertion tube; and control cables; the operating handle including: a housing; a control lever comprising a wall and trunnions extending laterally from the wall, the wall comprising a control lever immobilization aperture; a first wall comprising a first support aperture and a first immobilization aperture; a second wall comprising a second support aperture, the first support aperture and the second support aperture receiving the trunnions to facilitate rotation of the control lever, and the control lever immobilization aperture and the first immobilization aperture being alignable to receive a tool and thereby immobilize the control lever in a neutral position during attachment of the control cables to the control lever.

17 Claims, 12 Drawing Sheets

Related U.S. Application Data continuation of application No. 15/576,816, filed as application No. PCT/DK2016/050150 on May 26, 2016, now Pat. No. 10,645,260.

(51) Int. Cl.
*H04N 5/232* (2006.01)
*H04N 7/10* (2006.01)

(52) U.S. Cl.
CPC ..... *A61B 1/00142* (2013.01); *H04N 5/23293* (2013.01); *H04N 7/102* (2013.01); *A61B 1/00124* (2013.01); *H04N 2005/2255* (2013.01)

(56) References Cited

U.S. PATENT DOCUMENTS

| | | | |
|---|---|---|---|
| 4,203,430 A | 5/1980 | Takahashi | |
| 4,750,475 A | 6/1988 | Yoshihashi | |
| 4,757,827 A | 7/1988 | Buchbinder et al. | |
| 4,805,596 A | 2/1989 | Hatori | |
| 4,905,666 A | 3/1990 | Fukuda | |
| 5,167,221 A | 12/1992 | Chikama | |
| 5,275,151 A | 1/1994 | Shockey et al. | |
| 5,299,562 A | 4/1994 | Heckele et al. | |
| 5,373,317 A | 12/1994 | Salvati et al. | |
| 5,435,805 A | 7/1995 | Edwards et al. | |
| 5,450,851 A | 9/1995 | Hancock | |
| 5,462,527 A | 10/1995 | Stevens-Wright et al. | |
| 5,810,876 A | 9/1998 | Kelleher | |
| 5,879,289 A | 3/1999 | Yarush et al. | |
| 5,938,588 A | 8/1999 | Grabover et al. | |
| 6,007,531 A | 12/1999 | Snoke et al. | |
| 6,077,277 A | 6/2000 | Mollenauer et al. | |
| 6,258,101 B1 | 7/2001 | Blake, III | |
| 6,270,508 B1 | 8/2001 | Klieman et al. | |
| 6,390,972 B1 | 5/2002 | Speier et al. | |
| 8,790,250 B2 | 7/2014 | Petersen et al. | |
| 10,617,284 B2 | 4/2020 | Matthison-hansen | |
| 10,624,531 B2 | 4/2020 | Matthison-hansen | |
| 10,624,617 B2 | 4/2020 | Matthison-hansen et al. | |
| 10,631,716 B2 | 4/2020 | Matthison-hansen | |
| 10,645,260 B2 | 5/2020 | Matthison-hansen et al. | |
| 10,646,107 B2 | 5/2020 | Matthison-hansen et al. | |
| 10,779,710 B2 | 9/2020 | Matthison-Hansen | |
| 2002/0099266 A1 | 7/2002 | Ogura et al. | |
| 2003/0009176 A1 | 1/2003 | Bilitz | |
| 2005/0070764 A1 | 3/2005 | Nobis et al. | |
| 2005/0075539 A1 | 4/2005 | Schulz et al. | |
| 2005/0273085 A1 | 12/2005 | Hinman et al. | |
| 2006/0025651 A1 | 2/2006 | Adler et al. | |
| 2006/0173243 A1 | 8/2006 | Watanabe | |
| 2006/0258955 A1 | 11/2006 | Hoffman et al. | |
| 2007/0219411 A1 | 9/2007 | Dejima et al. | |
| 2007/0250038 A1 | 10/2007 | Boulais | |
| 2007/0282167 A1 | 12/2007 | Barenboym et al. | |
| 2008/0051631 A1 | 2/2008 | Dejima et al. | |
| 2008/0188868 A1 | 8/2008 | Weitzner et al. | |
| 2008/0195128 A1 | 8/2008 | Orbay et al. | |
| 2008/0249483 A1 | 10/2008 | Slenker et al. | |
| 2008/0287735 A1 | 11/2008 | Takemoto et al. | |
| 2009/0054733 A1 | 2/2009 | Marescaux et al. | |
| 2009/0076328 A1 | 3/2009 | Root et al. | |
| 2009/0209945 A1 | 8/2009 | Lobl et al. | |
| 2009/0247994 A1 | 10/2009 | Bacher et al. | |
| 2010/0022837 A1 | 1/2010 | Ishiguro et al. | |
| 2010/0030020 A1 | 2/2010 | Sanders et al. | |
| 2010/0249497 A1 | 9/2010 | Peine et al. | |
| 2010/0268268 A1 | 10/2010 | Bacher et al. | |
| 2010/0298642 A1 | 11/2010 | Trusty et al. | |
| 2011/0009694 A1 | 1/2011 | Schultz et al. | |
| 2011/0112517 A1 | 5/2011 | Peine et al. | |
| 2011/0264129 A1 | 10/2011 | Holdgate et al. | |
| 2011/0306831 A1 | 12/2011 | Koehnke et al. | |
| 2011/0306841 A1 | 12/2011 | Lozman et al. | |
| 2012/0116362 A1 | 5/2012 | Kieturakis | |
| 2014/0073855 A1 | 3/2014 | Kindler | |
| 2014/0142377 A1 | 5/2014 | Yang et al. | |
| 2014/0148759 A1 | 5/2014 | Macnamara et al. | |
| 2014/0206936 A1 | 7/2014 | Cooper et al. | |
| 2014/0221749 A1 | 8/2014 | Grant et al. | |
| 2014/0243615 A1 | 8/2014 | Schaeffer et al. | |
| 2014/0275763 A1 | 9/2014 | King et al. | |
| 2014/0316203 A1 | 10/2014 | Carroux et al. | |
| 2014/0336532 A1 | 11/2014 | Seguy | |
| 2015/0282701 A1 | 10/2015 | Oskin et al. | |
| 2015/0366436 A1 | 12/2015 | Iuel | |
| 2016/0095585 A1 | 4/2016 | Zergiebel et al. | |
| 2016/0150946 A1 | 6/2016 | Tsumaru et al. | |
| 2016/0348769 A1 | 12/2016 | Siegal | |
| 2018/0203316 A1 | 7/2018 | Xu | |
| 2018/0203317 A1 | 7/2018 | Li et al. | |
| 2018/0296068 A1 | 10/2018 | Matthison-Hansen et al. | |
| 2018/0296069 A1 | 10/2018 | Matthison-Hansen | |
| 2018/0303315 A1 | 10/2018 | Matthison-Hansen | |
| 2018/0303316 A1 | 10/2018 | Matthison-Hansen | |
| 2018/0303317 A1 | 10/2018 | Matthison-Hansen | |
| 2018/0303472 A1 | 10/2018 | Matthison-Hansen et al. | |
| 2018/0309908 A1 | 10/2018 | Matthison-Hansen et al. | |
| 2020/0229680 A1 | 7/2020 | Matthison-Hansen et al. | |
| 2020/0267292 A1 | 8/2020 | Matthison-Hansen et al. | |
| 2020/0352413 A1 | 11/2020 | Matthison-Hansen et al. | |

FOREIGN PATENT DOCUMENTS

| | | | |
|---|---|---|---|
| CN | 1956684 A | 5/2007 | |
| CN | 101513338 A | 8/2009 | |
| CN | 102871636 A | 1/2013 | |
| CN | 103505176 A | 1/2014 | |
| CN | 203506676 U | 4/2014 | |
| CN | 203885470 U | 10/2014 | |
| CN | 204120980 U | 1/2015 | |
| EP | 0567146 A2 | 10/1993 | |
| EP | 1484003 A1 | 12/2004 | |
| EP | 1561413 A1 | 8/2005 | |
| JP | 09-010166 A | 1/1997 | |
| WO | 2005/112806 A2 | 12/2005 | |
| WO | 2008/033356 A2 | 3/2008 | |
| WO | 2008/045374 A2 | 4/2008 | |
| WO | 2008/061106 A1 | 5/2008 | |
| WO | 2010/066789 A1 | 6/2010 | |
| WO | 2010/066790 A1 | 6/2010 | |
| WO | 2013/071938 A1 | 5/2013 | |
| WO | 2013/106444 A1 | 7/2013 | |
| WO | 2014/127780 A1 | 8/2014 | |

OTHER PUBLICATIONS

Danish Patent and Trademark Office Action for Appl No. PA201570321 dated Sep. 3, 2015, 3 pages.
Danish Patent and Trademark Office Search Report for Appl No. PA201570317 dated Aug. 25, 2015, 6 pages.
Danish Patent and Trademark Office Search Report for Appl No. PA201570318 dated Aug. 27, 2015, 4 pages.
Danish Patent and Trademark Office Search Report for Appl No. PA201570319 dated Aug. 31, 2015, 9 pages.
Danish Patent and Trademark Office Search Report for Appl No. PA201570320 dated Oct. 21, 2015, 7 pages.
Danish Patent and Trademark Office Search Report for Appl No. PA201570321 dated Sep. 2, 2015, 2 pages.
Danish Patent and Trademark Office Search Report for Appl No. PA201570322 dated Aug. 25, 2015, 7 pages.
Danish Patent and Trademark Office Search Report for Appl No. PA201570323 dated Jul. 9, 2015, 8 pages.
EPC communication in related EP appl. No. 16 726 777.A, dated Sep. 25, 2018; 2 pgs.
Examination report in related Chinese application No. 2016800384403, dated Dec. 28, 2018, 11 pgs.
Examination report in related Chinese application No. 201680038859.9 dated Aug. 2, 2019, 9 pgs.
Examination report in related Chinese application No. 2016800388599 dated Dec. 28, 2018, 9 pgs.

(56) References Cited

OTHER PUBLICATIONS

Examination report in related Chinese application No. 201680038906X dated Nov. 26, 2018, 6 pgs.
Examination report in related Chinese application No. 2016800390616, dated Dec. 28, 2018, 9 pgs.
Examination report in related Chinese application No. 2016800390902 dated Dec. 11, 2018, 9 pgs.
Examination report in related Chinese application No. 2016800390902 dated Jul. 15, 2019, 4 pgs., including summary translation from Chinese counsel.
Examination report in related Chinese application No. 201680039147.9, dated Dec. 28, 2018 and translation from examiner.
Examination report in related Chinese application No. CN201680036584.5, dated Nov. 12, 2018; 8 pgs.
Examination report in related European application No. 16726776.4, dated Dec. 23, 2020, 4 pgs.
International Preliminary Report on Patentability received for PCT Patent Application No. PCT/DK2016/050148, dated Dec. 7, 2017, 7 pages.
International Preliminary Report on Patentability received for PCT Patent Application No. PCT/DK2016/050149, dated Dec. 7, 2017, 7 pages.
International Preliminary Report on Patentability received for PCT Patent Application No. PCT/DK2016/050150, dated Dec. 7, 2017, 7 pages.
International Preliminary Report on Patentability received for PCT Patent Application No. PCT/DK2016/050151, dated Dec. 7, 2017, 8 pages.
International Preliminary Report on Patentability received for PCT Patent Application No. PCT/DK2016/050153, dated Dec. 7, 2017, 9 pages.
International Preliminary Report on Patentability received for PCT Patent Application No. PCT/DK2016/050154, dated Dec. 7, 2017, 8 pages.
International Search Report for PCT/DK2016/050148 dated Aug. 11, 2016, 5 pages.
International Search Report for PCT/DK2016/050150 dated Aug. 1, 2016, 5 pages.
International Search Report for PCT/DK2016/050150 dated Aug. 11, 2016, 5 pages.
International Search Report for PCT/DK2016/050151 dated Aug. 9, 2016, 5 pages.
International Search Report for PCT/DK2016/050152 dated Aug. 5, 2016, 5 pages.
International Search Report for PCT/DK2016/050153 dated Aug. 9, 2016, 4 pages.
International Search Report issued in PCT/DK2016050149, dated Aug. 5, 2016, 4 pages.
International Search Report issued in PCT/DK2016050154, dated Aug. 8, 2016, 7 pages.
Office Action dated Jan. 13, 2020 in Chinese application No. 201680036584.5 with translation of content.
Office Action in corresponding Chinese application No. 201680036584 dated Jul. 22, 2019, 5 pgs., including summary translation from Chinese counsel.
Office Action in corresponding Chinese application No. 201680039061 dated Aug. 2, 2019, 6 pgs., including summary translation from Chinese counsel.
Office Action in corresponding Chinese Application No. 201680039061, dated Sep. 27, 2020, including English summary from Chinese counsel; 6 pages.
Office Action in corresponding Chinese application No. 201680039147 dated Aug. 2, 2019, 9 pgs., including summary translation from Chinese counsel.
Search Report issued by the Chinese Patent Office, dated Mar. 3, 2020, for related Chinese Patent Application No. 201680038859.9; 9 pages.
Search Report issued by the Chinese Patent Office, dated Mar. 3, 2020, for related Chinese Patent Application No. 201680039061.6; 10 pages.
Search Report issued by the European Patent Office, dated Jun. 17, 2020 for related Application No. 16 726 778.0; 5 pages.
Written Opinion ISA for PCT/DK2016/050148 dated Aug. 10, 2016 in European Register, 46 pages.
Written Opinion of the International Searching Authority for PCT/DK2016/050149 dated Aug. 4, 2016 in European Register, 5 pages.
Written Opinion of the International Searching Authority for PCT/DK2016/050150 dated Aug. 10, 2016 in European Register, 5 pages.
Written Opinion of the International Searching Authority for PCT/DK2016/050151 dated Aug. 8, 2016 in European Register, 6 pages.
Written Opinion of the International Searching Authority for PCT/DK2016/050152 dated Aug. 4, 2016 in European Register, 6 pages.
Written Opinion of the International Searching Authority for PCT/DK2016/050153 dated Aug. 8, 2016 in European Register, 7 pages.
Written Opinion of the International Searching Authority for PCT/DK2016/050154 dated Aug. 4, 2016 in European Register, 6 pages.

ENDOSCOPE

CROSS-REFERENCE TO RELATED APPLICATIONS

The present application is a continuation of U.S. patent application Ser. No. 16/860,831, filed Apr. 28, 2020, which is a continuation of U.S. patent application Ser. No. 15/576,816, issued as U.S. Pat. No. 10,645,260 on May 5, 2020, which is a § 371 application of International Application Number PCT/DK2016/050150, filed May 26, 2016, which claims priority from Denmark Patent Application Number PA 2015 70319, filed May 27, 2015, all said applications incorporated herein by reference in their entirety.

The following applications disclose related subject matter: U.S. patent application Ser. No. 15/576,812, issued as U.S. Pat. No. 10,646,107 on May 12, 2020; U.S. patent application Ser. No. 15/576,813, issued as U.S. Pat. No. 10,631,716 on Apr. 28, 2020; U.S. patent application Ser. No. 15/576,814, issued as U.S. Pat. No. 10,624,531 on Apr. 21, 2020; U.S. patent application Ser. No. 15/576,815, issued as U.S. Pat. No. 10,617,284 on Apr. 14, 2020; U.S. patent application Ser. No. 15/576,817, issued as U.S. Pat. No. 10,624,617 on Apr. 21, 2020; U.S. patent application Ser. No. 15/576,818, issued as U.S. Pat. No. 10,779,710 on Sep. 22, 2020; and U.S. patent application Ser. No. 16/839,991, filed Apr. 3, 2020.

TECHNICAL FIELD

The present invention relates to an endoscope, in particular but not exclusively a disposable camera endoscope, having an operating handle arranged at a proximal end thereof and an insertion tube extending from said handle towards a distal end of the endoscope.

BACKGROUND

In general, an endoscope comprises an operating handle at the proximal end and an insertion tube extending from the handle towards the distal end. The handle is adapted to be held by an operator and inter alia comprises externally protruding operating members connected to internal control means allowing the operator to control the motion of the distal end of the insertion tube, while advancing the distal end of the insertion tube to a desired location e.g. within a body cavity of a person. Examples of such endoscopes are disclosed in WO2013/071938A1 and WO2010/066789A1.

In modern endoscopes the tip forming the distal end of the insertion tube comprises a camera and illumination means allowing the operator to see his actions on a monitor connected to the endoscope. This necessitates supply and signal cables to be drawn between the tip and the monitor. In the tip space is very limited and generally there is no or little room for electronics, such as an amplifier. The signals from the imaging chip of the camera may thus not be amplified at the source. Transmitting directly weak signals all the way to the monitor, is undesirable because weak signals are more prone to disturbances from noise picked up by long cables, than stronger signals would be. Moreover, weak signals may be prone to attenuation in connectors in the signal path, e.g. the plug and socket connection to the monitor, and would thus require expensive high quality connectors.

It is thus desirable to interpose amplification and signal processing means in the signal path from the tip of the insertion tube to the monitor, preferably at a location where more space is available, such as in the handle of the endoscope.

In the handle, however, there may in some clinical situations be a risk of undesired contact with fluids. Main problem is water, which may disturb or ruin the electronics, in particular aqueous saline solutions, but other electrolytes may also pose problems.

It is therefore necessary to protect the electronics in a protected manner, sealed from such fluids.

SUMMARY

According to the present invention this object is achieved by an endoscope having an operating handle comprising a handle housing arranged at a proximal end thereof, an insertion tube extending from said handle towards a distal end of the endoscope, and a sealed compartment adapted to accommodate electronic circuitry of the endoscope and arranged at least partially within said handle housing, characterized in that said compartment furthermore comprises a cable conduit extending from said mounting plate towards the distal end of the endoscope, said conduit being terminated in a sealing manner at the distal end of the endoscope.

This has multiple advantages. Main advantage is that having a dedicated sealed compartment obviates the need of sealing the outer handle housing, which itself is difficult because the housing must allow for movable parts such as the operating buttons to protrude through the handle housing. In particular, it provides a single sealed compartment in which the electrical cables to the camera in the tip of the endoscope are also protected from undesired fluids. Despite this fact, the outer housing does provide some shielding and to some extent a two layer barrier against influx of undesired fluids is thus provided. Furthermore, because the inner compartment is not subject to the same ergonomical constraints as the outer housing, it is much easier do design a joint which is easy to seal, e.g. follows straight lines, than a joint between ergonomically shaped outer housing parts. Finally, because the inner compartment is much smaller than the outer housing the joints will be much shorter and thus easier to seal, i.e. less prone to bad gluing or welding as the case may be.

According to a preferred embodiment the sealed compartment comprises a mounting plate adapted to carry said electronic circuitry, and a cover connected to the mounting plate, so as to enclose the electronic circuitry. The mounting plate and the cover may thereby be devised to join each other in a plane, and may thus be designed with easily joined straight lines.

According to a further preferred embodiment, the operating handle comprises a shell structure. Using a shell structure with several shell parts facilitates the assembly of the endoscope, and in particular access to inner components in the handle when mounting them.

According to a further preferred embodiment, the operating handle comprises an inner, essentially shell shaped chassis having a shell structure with a shell wall with an inner surface and an outer surface linked by an edge, said shell structure defining an interior compartment delimited by said inner surface and the edge of the shell wall, the edge thus defining main opening of said interior compartment, and in that the mounting plate is adapted to engage said shell shaped chassis in the vicinity of the edge, so as to partially cover said inner compartment. In this way the mounting plate may be used to stabilize and increase the rigidity of the shell shaped chassis, in turn allowing the shell shaped chassis to be weakened by apertures provided in the wall and or by the use of a further reduced wall thickness, be it localised or overall.

According, to another preferred embodiment the mounting plate comprises a number of flanges adapted to extend into the interior compartment when the mounting plate is in engagement with said chassis and partially covers the inner compartment. Providing such flanges allow the separation between inner parts. In particular movable ones, such as control cables, may be kept separate from other parts which may be prone to damage from the moving cables.

According to a further preferred embodiment, the cable conduit is accommodated within an outer sheath of the insertion tube. Thereby additional protecting against undesired fluids is provided.

According to yet another preferred embodiment, at least one of said mounting plate or said cover is made from a transparent plastic material. If one, or preferably both of said mounting plate and said cover is made from transparent material, the two parts may efficiently be sealed along the joint by the use of UV curing glue or resin. Likewise applies to the joining of the mounting plate to the chassis if desired.

A person skilled in the art will appreciate that any one or more of the above aspects of this disclosure and embodiments thereof may be combined with any one or more of the other aspects of this disclosure and embodiments thereof.

BRIEF DESCRIPTION OF DRAWINGS

The present invention will now be described in greater detail based on non-limiting exemplary embodiments and with reference to the drawings, on which.

DETAILED DESCRIPTION

Figure 2:
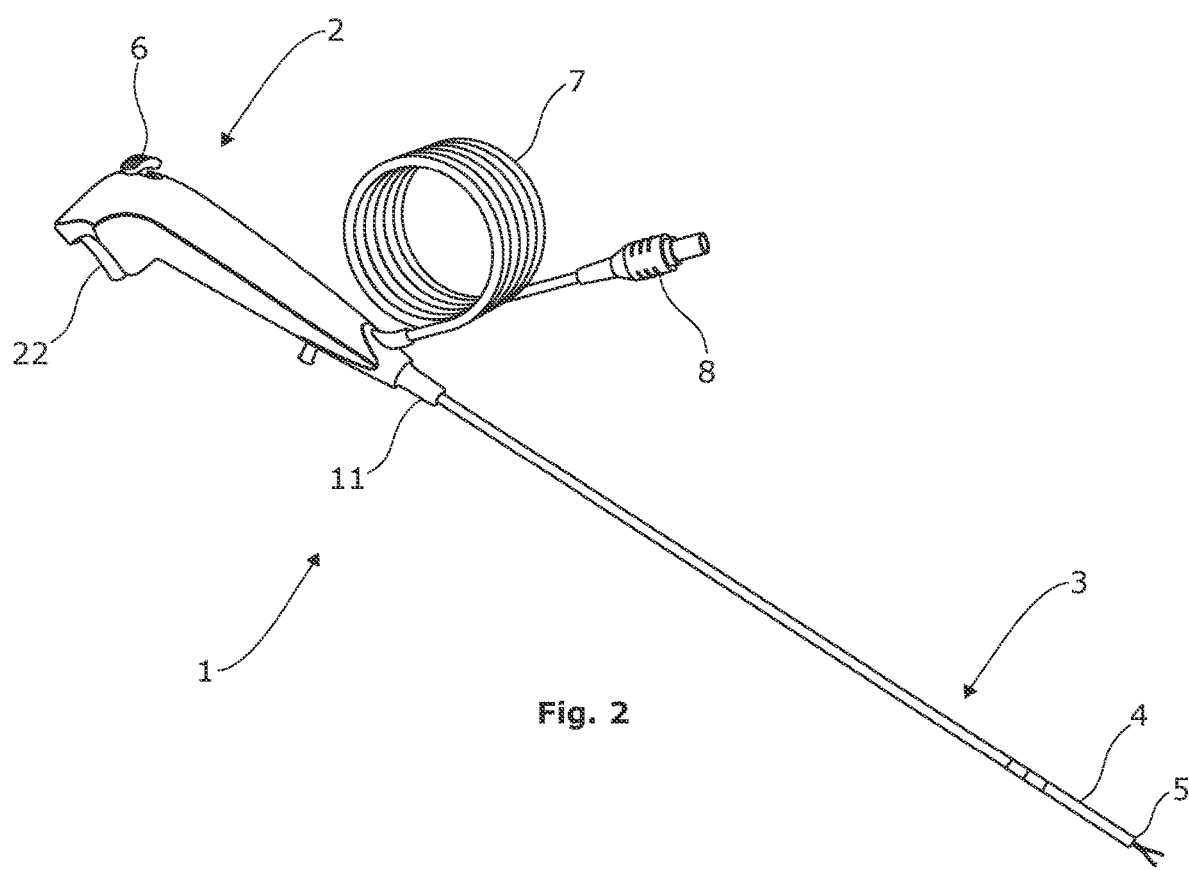
FIG. 2 shows a perspective view of the fully assembled endoscope of FIG. 1.
Figure 3:
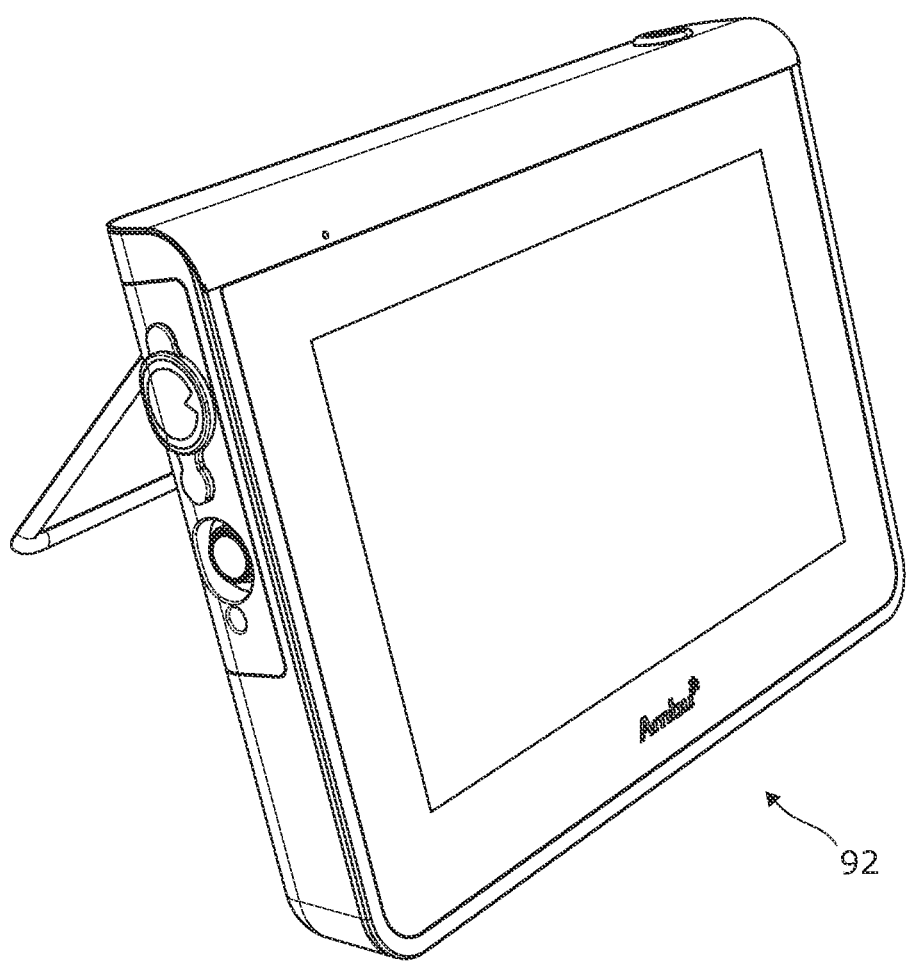
FIG. 3 shows a monitoring device adapted for mutual connection with the endoscope of FIG. 1.

Turning first to FIG. 2 an assembled endoscope 1 according to the present invention is shown. The endoscope 1 has a proximal end with an operating handle 2 to be held in one hand by an operator. Accordingly, the operating handle is shaped in a manner ergonomically suitable for operator, in particular but not exclusively for the hand of the operator, as arms and joints may also play a role in the ergonomics. From the handle 2 an insertion tube 3 extends towards the distal end of the endoscope. At the distal end of the endoscope 1 the insertion tube 3 ends in a bending section 4 and a tip part 5. The bending section 4 is in mechanical connection with an operating member 6, digitally operable by the operator, e.g. by the thumb, thereby allowing the operator to bend the tip part 5 in a desired direction when advancing the insertion tube 3 towards a desired location, e.g. through a body cavity of a patient. As can also be seen the endoscope 1 comprises a flexible connection cable 7 with a connector 8 allowing the endoscope 1 to be connected to a monitoring device such as a monitor 92 shown in FIG. 3 forming part of an endoscope 1 and monitor 92 system.

Figure 1:
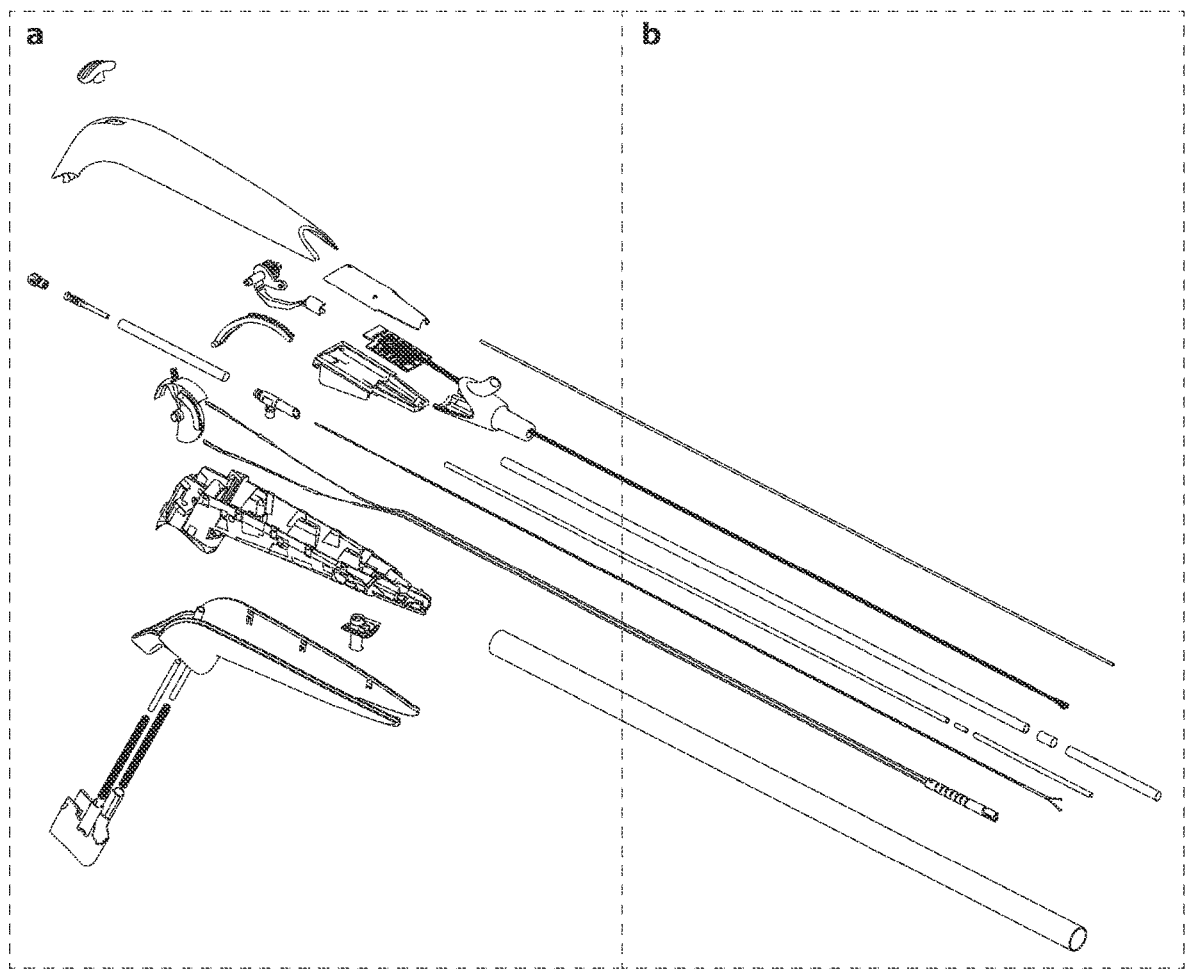
FIG. 1 shows an exploded overview of an endoscope according to the present invention and how this exploded view is split in a left-hand side part and a right-hand side part for better visibility in FIG. 1a and FIG. 1b.
Figure 1A:
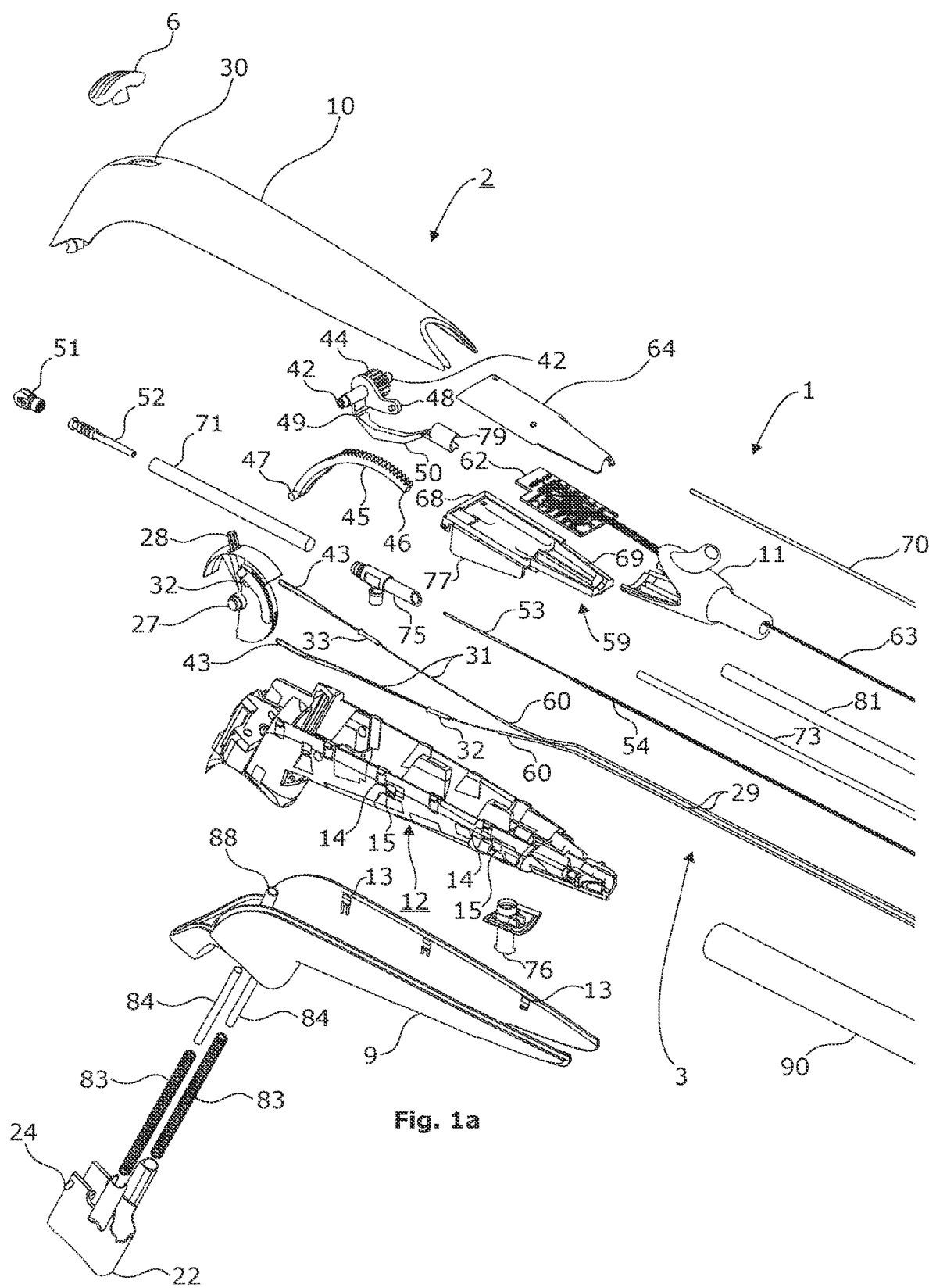
Figure 1B:
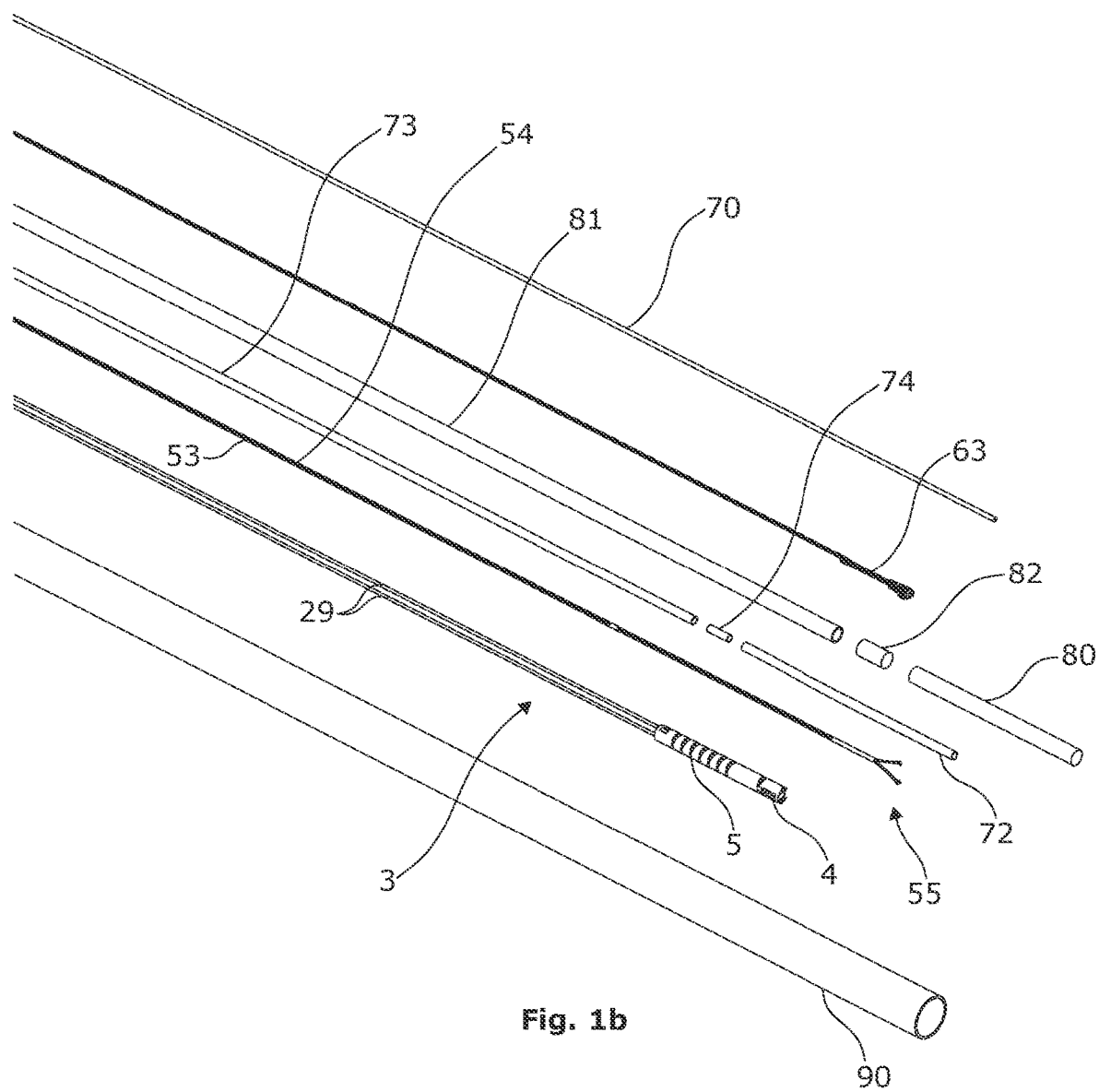

Turning now to FIGS. 1, 1a and 1b, an exploded view of the endoscope 1 is shown. As mentioned, the endoscope 1 has an operating handle 2 at the proximal end thereof i.e. at the left-hand side of FIG. 1a. The operating handle 2 is assembled from and comprises a number of handle parts to be described later. From the operating handle 1, the insertion tube 3 comprising a number of insertion tube parts to be described later extends towards the distal end of the endoscope, i.e. towards the right-hand side of FIG. 1b.

As can be seen in FIG. 1a, the operating handle 2 comprises at least two shell parts 9, 10 forming the outer housing walls of the handle housing of the operating handle 2. The two shell parts 9, 10 form the outer housing walls and are shaped to provide an ergonomically suitable operating handle for an operator, gripping it with one hand. In addition to the two shell parts 9, 10 a transition part 11 forming the transition from the operating handle to the insertion tube 3, may be provided. This transition part may also form part of the handle housing. However, the two shell parts 9, 10 constitute the major part of the housing in the embodiment shown.

Figure 4:
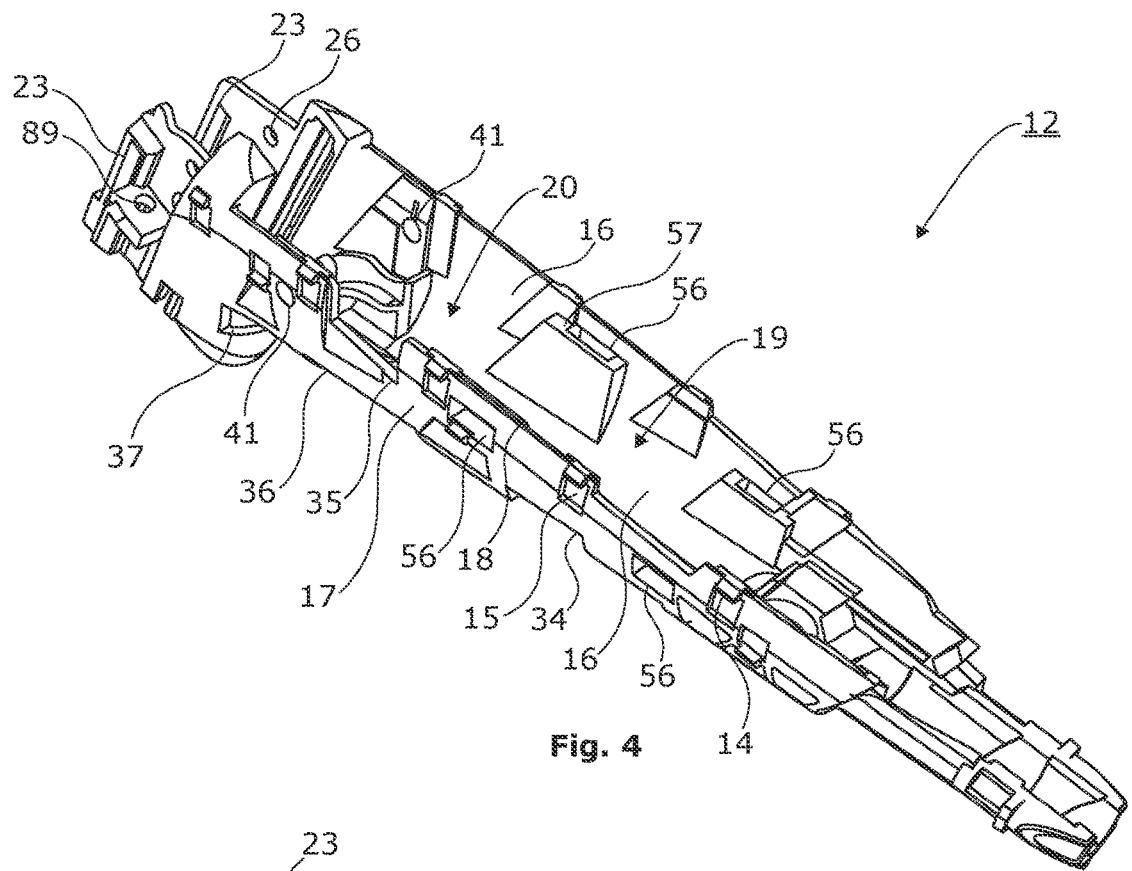
FIG. 4 shows a first perspective view of a chassis of the endoscope of FIG. 1.
Figure 5:
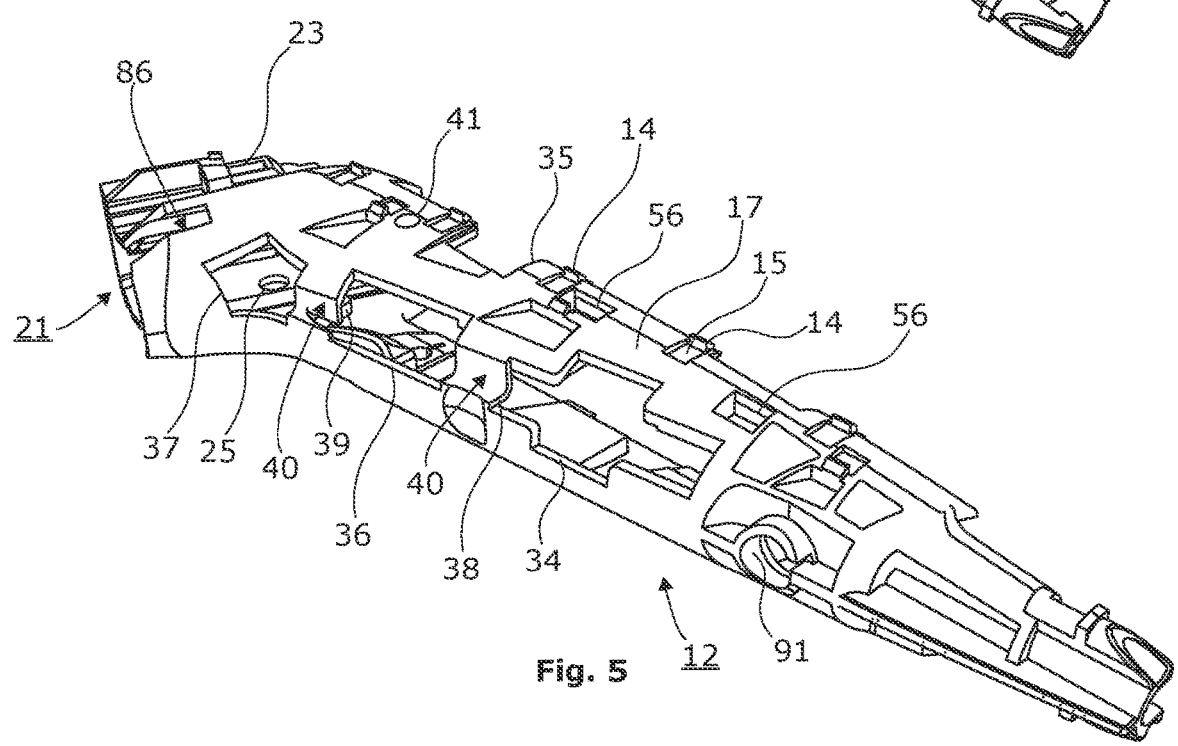
FIG. 5 shows a second perspective view of the chassis of FIG. 4.

The two shell parts 9, 10 are adapted to engage and be held and be supported by a chassis 12, in turn, adapted to support said at least two shells parts 9, 10 by suitable engagement means, such as recesses and/or protrusions 13 interlocking with suitable complementary means 14, 15 on the chassis 12, better visible in FIGS. 4 and 5. Furthermore the shell part 10 has pair of columns 88 of which only one is visible in FIG. 1a. These columns 88 serve the attachment of the shell part 10 to the chassis 12. The shell part has internal engagement means (not visible) adapted to engage the shell part 9 at the proximal end of the endoscope 1, so as hold them together. At the other end the shell parts are held together by the transition part 11.

Turning now to the FIGS. 4, 5 and 6, the chassis 12 will be described in greater detail. The chassis 12 preferably shell shaped, i.e. said chassis comprises an essentially shell shaped structure with a shell wall having an inner surface 16 and an outer surface 17 linked by an edge 18, said essentially shell shaped structure defining an interior compartment 19 delimited by said inner surface 16 and the edge 18 of the shell wall, the edge thus defining main opening 20 of said interior compartment 19. It will be understood that the chassis 12 can be designed mainly based on technical requirements, such as kinematic chains of movable parts, and thus be optimized for those technical requirements without having to inherit constraints from the ergonomic requirements of the handle 2, i.e. the shape of the two shell parts 9, 10.

Best visible in FIGS. 4 and 5 are a number of different apertures and cut-outs formed in the chassis 12. These apertures form vias for different purposes between the interior compartment 19 and the exterior of the chassis 12.

The different cut-outs and apertures differ in shape, size, location and layout depending on their purposes, and may as mentioned be designed according to technical requirements, independently of the ergonomic requirements of the handle 2.

Figure 6:
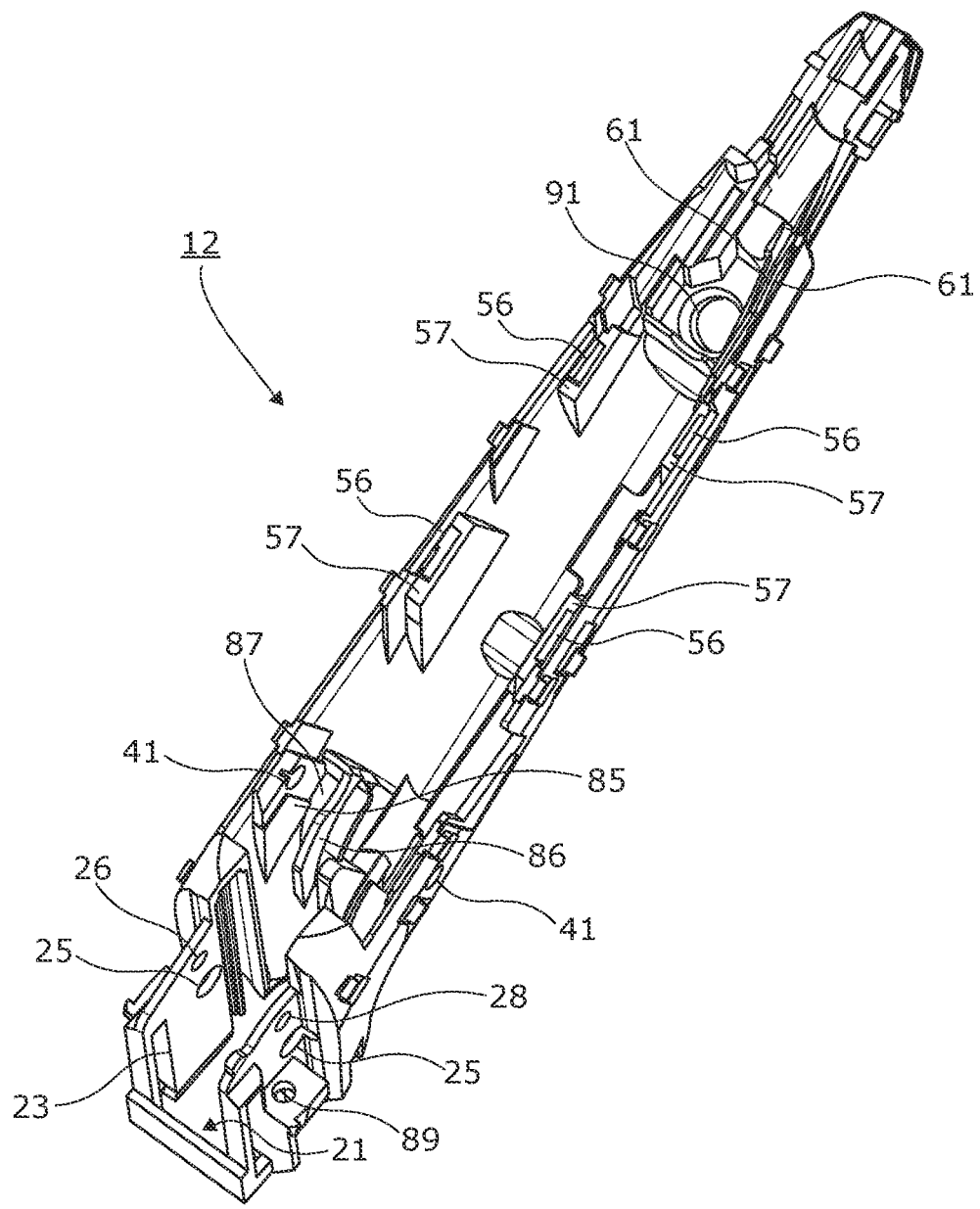
FIG. 6 shows a third perspective view of the chassis of FIG. 4.

Starting from the proximal end of the endoscope 1 there is an aperture 21, as best seen in FIG. 6. The aperture 21 accommodates a push button 22, so that the push-button 22 extends from the interior compartment of the chassis 12 to the exterior, and on through an aperture in the shell part 9 to be accessible by an operator holding the handle 2 of the endoscope 1. The push-button 22 is preferably biased towards an external position by means of two coil springs 83 guided by two guiding columns 84 fixed in the bottom two wells provided in the chassis 12, preferably by gluing using UV-curable glue or resin transmitted through the transparent material of the chassis 12. The two guiding columns 83 further serve to reduce friction between the coil springs 83 and the columns 88. They are therefore preferably made of a material with relatively low friction, such as low-density polyethylene LDPE, e.g. Comothene® 4812.

On the outer surface 17 of the shell wall of the chassis 12 two lugs with holes 89 are provided. These serve to engage the columns 88 on the shell part 10 for attaching it to the chassis, as described above.

In the shell wall two elongate apertures 23 in the form of slits are provided. The two elongate apertures 23 are preferably arranged as a pair, one on either side of the aperture 23. The two elongate apertures 23 serve as guide means for the push-button by accommodating a respective protrusion 24 provided on the surface of the push-button 22.

In the vicinity of the two elongate apertures 23, a first and a second pair of apertures 25, 26 in the form of essentially cylindrical through holes are provided. The first pair of essentially cylindrical apertures serve as pivotal bearings for trunnions 27 of a control lever 28 for maneuvering the bending section 5 via a pair of Bowden pulls 29. As can best be seen in FIGS. 1 and 2, the control lever 28 is attached to the control knob 6, and at least the control knob extends to the outside of the endoscope handle 2 through a slit 30 in the shell part 10 to be accessible by a thumb of the an operator. It should be noted that it is not essential for the function as bearings for the trunnions 27 of the control knob, that the holes are though holes, but because the chassis is preferably injection moulded, through holes may be much easier manufactured than e.g. blind holes.

It will be understood that due to the slit 30 and other necessary openings in the shell parts 9, 10, the handle housing does not protect the internal components fully. Though some protection against spray and splash is provided by the shell parts 9, 10 there is basically fluid communication between the exterior and the interior of the handle housing. This is largely intended, as sealing these openings would be unnecessarily complicated and costly.

The second pair of apertures 26 are preferably also circular through holes and have the same diameter. They need not be circular, however, as their purpose is allowing the insertion of a tool, such as a rod in order to immobilise the control lever 28 during assembly of the endoscope, more specifically when attaching the proximal ends of the cables 31 of the two Bowden pulls 29 to the control lever 28. Accordingly, the control lever 28 has a through hole 32, corresponding in size to the apertures 26, and adapted to align with these in one position of the control lever 28, thereby allowing the insertion of the tool through all three holes, 26, 32, so as to block movement of the control lever 28 with respect to the chassis 12. The position of the three holes 26, 32 are selected so as to block the control lever 28 in a position later corresponding to a neutral position of the control lever 28 and knob 6, in which the bending section 4 is straight.

With the control lever 28 blocked during assembly the cables 31 Bowden pull may be attached to the control lever 28 in a well defined manner. This is preferably done by threading the respective free end of each cable 31 through suitable passages in the control lever 28, forming a loop 43 by looping the free ends back to the respective cable and crimping the free end onto the cable 31 using a barrel 33. The barrel 33 may be of the open barrel type, to avoid the hazel of sliding the barrel 33 on onto the cable 31 prior to crimping. Evidently, other attachments for the loop 43, such as protrusions, may also be used. Furthermore, entirely different attachments methods without loops are also envisaged, albeit not preferred.

To facilitate this assembly process a cross-shaped aperture 34 is located in the vicinity of the bottom of the chassis 12, i.e. away from the main opening 20 defined by the edge 18. Likewise a cut-out 35 in the wall from the edge 18 is provided. The cross-shaped aperture 34 and the cut-out 35 allows access to the cables 31 various tools, such as holding and crimping tools during the assembly.

Figure 7:
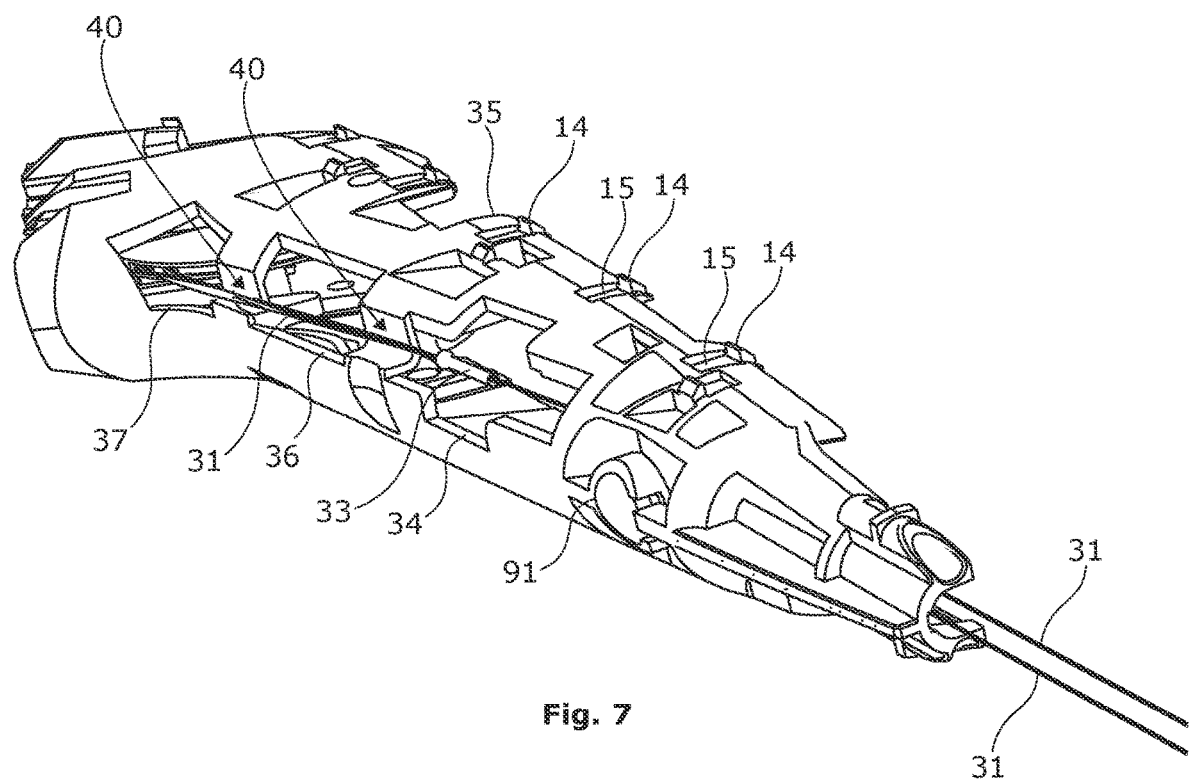
FIG. 7 shows a perspective view of the chassis of FIG. 4 with control cables and a control member mounted.
Figure 8:
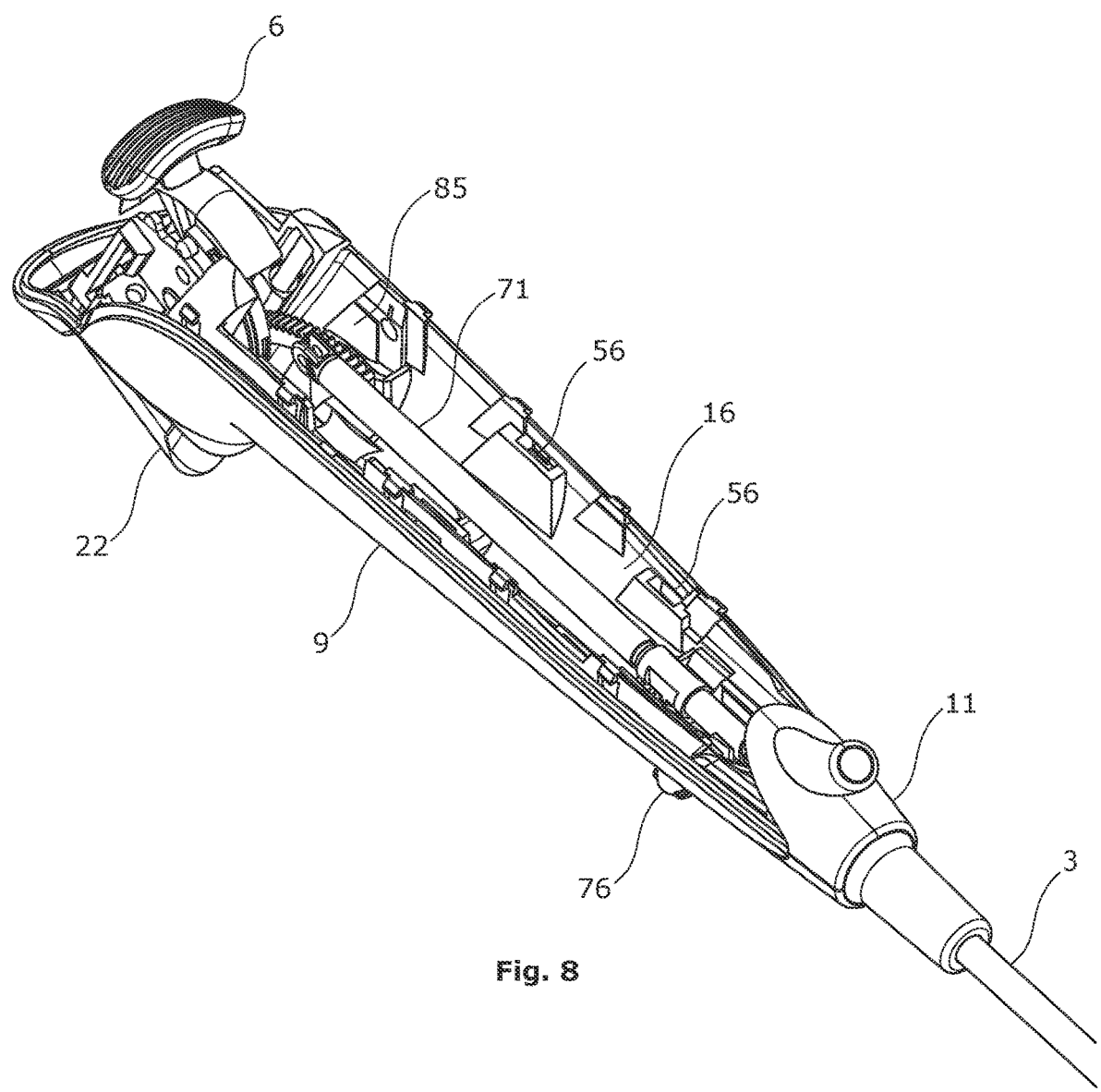
FIG. 8 shows a semi-assembled endoscope according to the invention with the chassis, movable parts and a housing shell part.

As can best be seen in FIG. 5 the cross-shaped aperture 34 a further, essentially rectangular aperture is generally aligned with a further rectangular access aperture 36 and a pentagonal aperture 37 in the direction towards the proximal end of the endoscope 1. The cross-shaped aperture 34, the rectangular aperture 36 and the pentagonal aperture 37 are separated by respective bridges 38 and 39. These bridges 38, 39 do not follow the general curvature of the outer surface 17 of the chassis 12 but are indented to form a generally V-shaped groove 40 connecting the cross-shaped aperture 34 to the pentagonal aperture 37 via the rectangular aperture 36. As can be seen from FIG. 7, this V-shaped groove 40 in the outer surface 17 provides the outer surface 17 with a means for guiding one or more movable parts, in particular the cable 31 of the Bowden pull between two apertures, such as the cross-shaped aperture 34 and the pentagonal aperture 37 along the outer surface 17 outside of the interior compartment 19. This in turn allows the unsupported free end of the cable 31 of the Bowden pull to follow a straight line. At the same time, because the unsupported free end of the cable 31 passes from the interior compartment 19 of the chassis 12 to the exterior via the cross-shaped aperture 34, the cable 31 becomes easily accessible for the assembly tools, in particular the crimping tool. The cross-shape of the cross-shaped aperture, in turn, facilitates the use of the tools by providing the necessary space for opening and closing the tools, be it a crimping tool or a holding tool.

In FIGS. 4 and 5 a further pair apertures 41 in the form of essentially cylindrical through holes can be seen. Similar to the apertures 25, the further pair of apertures 41 serve as bearings of trunnions 42 carrying a pinion 44. The pinion 44 is adapted to be in engagement with a curved rack 45 having a first free end 46 and a second end with trunnions 47 held loosely in suitable receptacles inside the push button 22. The rack 45 as such is loosely held in a guideway comprising a first side 85, a second side 86 and a curved bottom 87 adapted to keep the rack 45 in engagement with the pinion 44, cf. FIG. 6. The first side 85 and the second side 86 as well as the curved bottom 87 are preferably formed integrally with the remainder of the chassis 12, e.g. in an injection moulding process. The first side is preferably constituted by a plane surface of a thickened part of the wall, i.e. a raised part of the inner surface 16 of the chassis 12.

Rotation of the pinion 44 may be effected by an operator moving the push-button 22, e.g. depressing it using an index finger, upon which the push-button transfers motion to the curved rack, in turn rotating the pinion 44.

On the pinion 44, two lever arms 48 and 49 of different lengths are provided. These arms 48 and 49 are in rigid connection with the pinion 44. Via a number of intermediate parts 50, 51, 52, 53 and 54 a desired operation of a tool 55 at the tip part 4 at the distal end of the endoscope 1 may be effected when the pinion 44 is rotated. The manner in which the operation of the tool 55 is to be effected may depend on the details of the tool. Variations in requirements can be controlled in dependence on the differences in lengths of the lever arms 48 and 49, and possibly articulations of the intermediate part 50, at the design stage of the endoscope 1 with a tool for a specific purpose.

Figure 9:
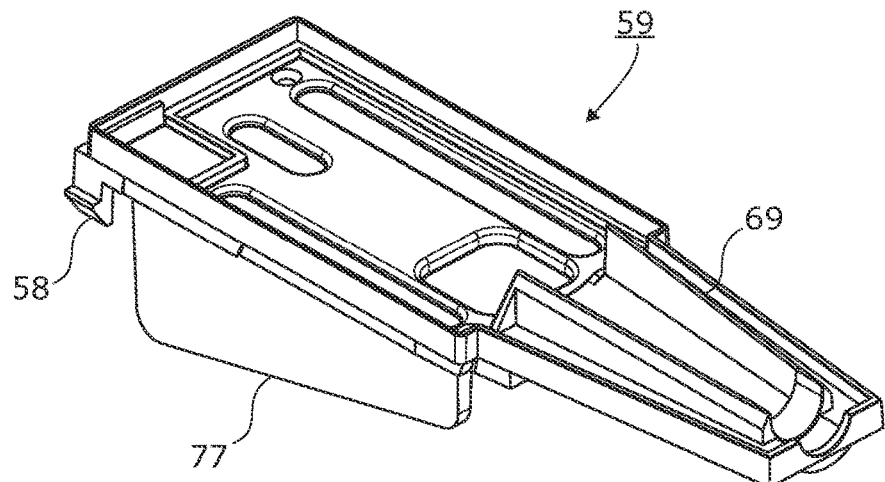
FIG. 9 shows a top perspective view of a mounting plate for carrying electronics of the endoscope.
Figure 10:
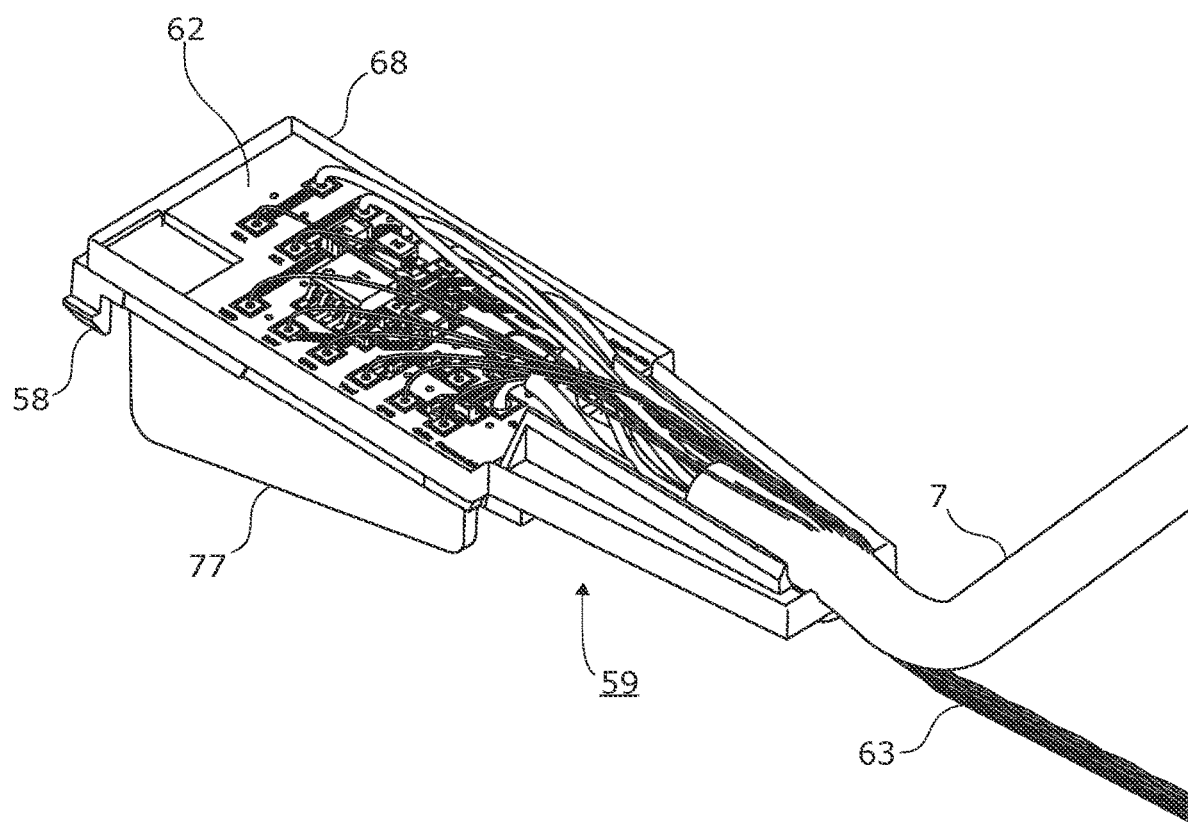
FIG. 10 shows the mounting plate carrying the electronics of the endoscope with electrical wiring extending therefrom.
Figure 11:
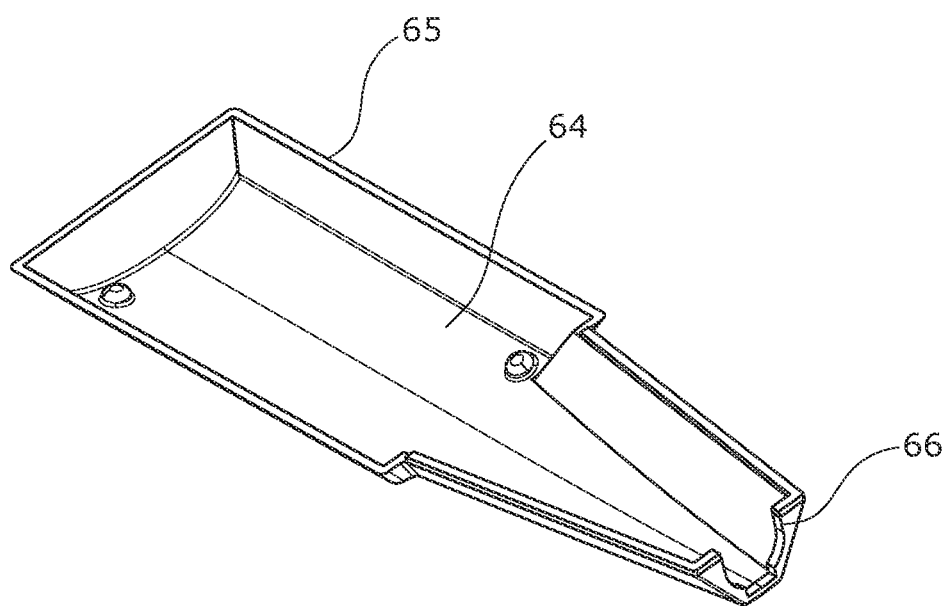
FIG. 11 shows bottom perspective view of a cover adapted to fit the mounting plate of FIG. 9.
Figure 12:
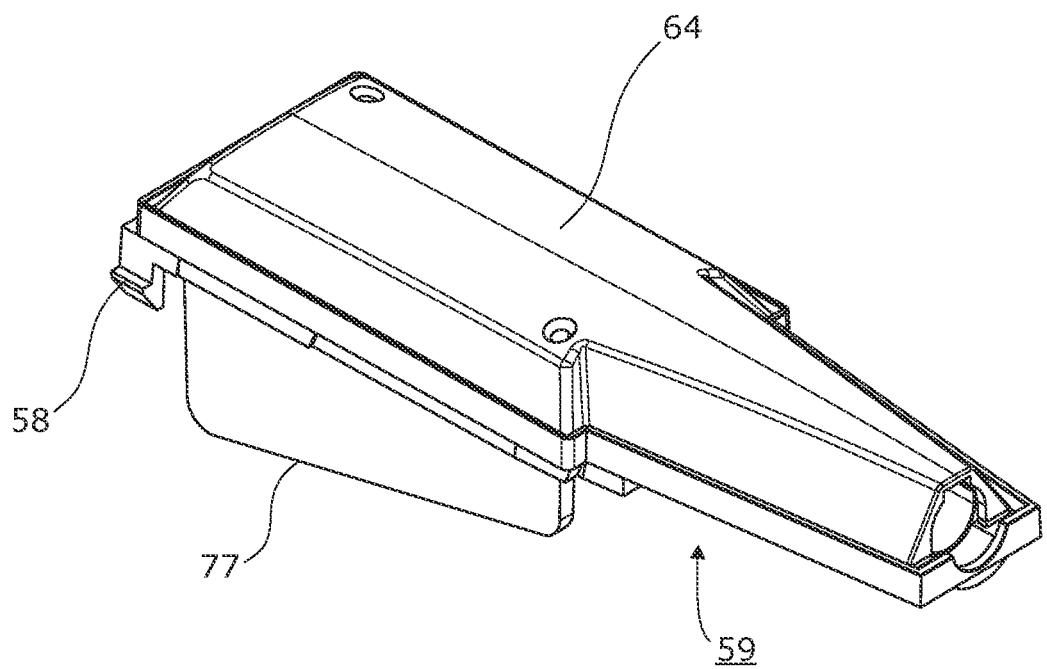
FIG. 12 shows a top perspective view of an assembly of the mounting plate of FIG. 9 and the cover of FIG. 11.
Figure 13:
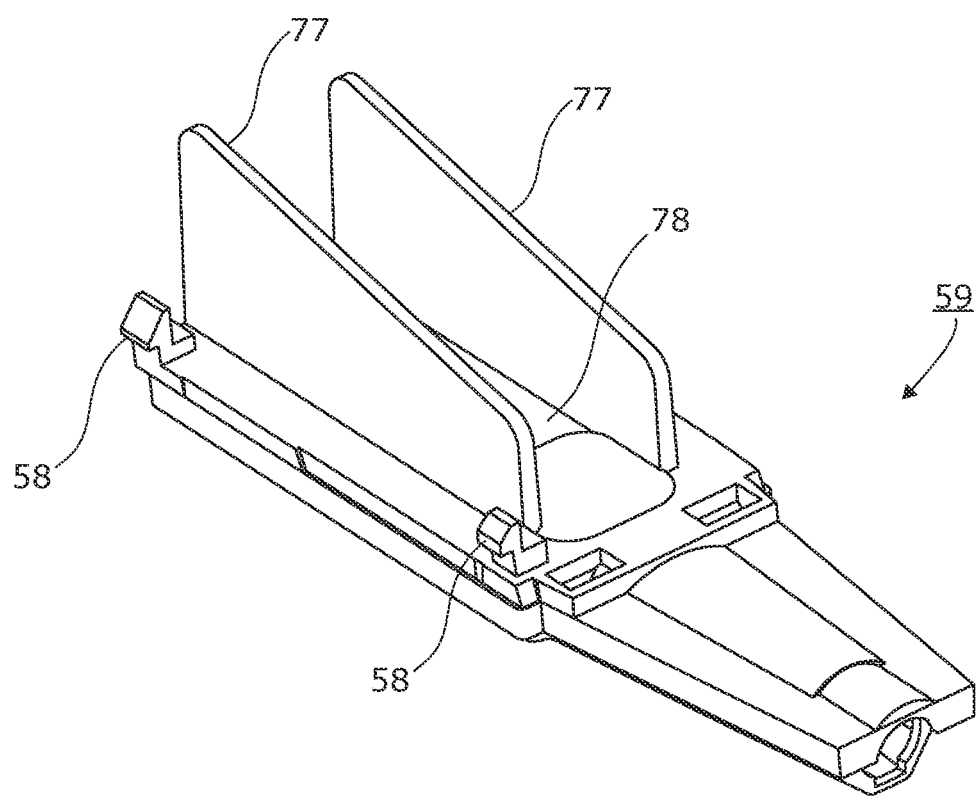
FIG. 13 shows a bottom perspective view of the assembly of FIG. 12.

As can best be seen in FIGS. 4 and 6 a number of apertures 56 are arranged to form openings from shelves 57 on the inner surface 16 of the chassis 12 to the outer surface 17 of the chassis 12. These openings are adapted to form undercut receptacles for protruding barbs 58 on a mounting plate 59 best seen in FIGS. 9, 10 and 13. The mounting plate 59 is preferably injection moulded from the same transparent plastic material as the chassis 12. Using a transparent plastic material is advantageous in that it allows parts to be joined and/or sealed using an UV curable glue or resin, i.e. one that hardens under the influence of ultraviolet light. In respect of glue or resin, be it UV curable or not, it has been found that simply gluing the proximal end portions of the outer tubes 60 of the Bowden pulls 29 in suitable recesses 61 provided along the inner surface 16 of the shell wall is sufficient to secure the Bowden pulls 29 in position. This is primarily, because, as it has been realized, adjustment is not needed. Adjustment, in turn, is not necessary because any slacking of the pull cable 31 of the Bowden pull 29 is negligible in a disposable endoscope 1. The pull cables 31 are not under any substantial tension during shelf life and will hardly undergo any mentionable stretching during the one short occasion the disposable endoscope 1 is in use.

The mounting plate 59 when attached to the chassis 12, and possibly secured thereto by preferably UC curing resin or glue, forms a partial lid over the main opening 20, and hence partially encloses the interior compartment 19. Closing the interior compartment partially on all four sides, rather than only three, adds rigidity to the chassis 12 as it hinders lateral compression, i.e. of the shell walls towards each other. Accordingly, the chassis 12 and in particular the walls parts thereof may be made with a reduced strength, i.e. thinner or with more or larger apertures than would otherwise be possible.

As the name suggest, the reinforcing of the chassis 12 it not the main purpose of the mounting plate 59. Rather, the mounting plate 59 is adapted to carry electronic circuitry of the endoscope 1, e.g. on a printed circuit board 62, as can best be seen in FIG. 10. In the following the electronic circuitry on the printed circuit board 62 will be referred to as main electronics. This is mainly to distinguish from other electronics located at or embedded in the tip 4 of the insertion tube 3 of the endoscope 1 which will accordingly be termed tip electronics. Both for the term main electronics and the term tip electronics it should be borne in mind that this description relates to a non-limiting exemplary embodiment, and that no functionality requirements should be attributed to these terms.

In modern camera endoscopes 1 the tip part 4 forming the distal end of the insertion tube 3 comprises a camera, such as a CCD camera, and illumination means, such as an LED, allowing the operator to see his actions on a monitor 92 connected to the endoscope 1. This necessitates supply and signal cables or wires 7, 63 to be drawn between the tip part 4 and the monitor 92. In the tip part 4 space is very limited and apart from the camera and illumination means there no or little room for electronics, such as an amplifier. The signals from the imaging chip of the camera may thus not be amplified at the source. Therefore the weak electrical analogue signals from the camera which are prone to disturbance by electrical noise picked up by signal wires, cables etc. on the way to the monitor 92. To overcome this, the main electronics acts as an intermediate between the tip electronics electrical power supply and amplification. Thus the weak signals from the camera arriving on the wires 63 may be amplified and otherwise modified, e.g. digitally encoded before they are transmitted to the monitor 92 via the flexible external connection cable 7. The present invention thus takes advantage of the fact that in the handle 2 of the endoscope 1 there is much better room for the amplification and signal processing means than anywhere else in the signal path from the tip part 4 at the distal end of the insertion tube 3 to the monitor 92.

Furthermore, with the main electronics being located on the mounting plate 59 in conjunction with the chassis 12 it becomes possible to accommodate the electronics according to technical requirements, without much consideration to ergonomic properties and the general layout of the handle 2. One particular technical requirement is the protection of the electronics against undesired contact with fluids such as water, which may disturb or ruin the electronics, in particular aqueous saline solutions. Other electrolytes may also pose problems, but main problem is water which in many clinical situations is ubiquitous. The traditional approach in multiple-use endoscopes as well as in single use, i.e. disposable endoscopes 1 has been to seal the outer housing. This, however, is difficult and costly because the integrity of the housing needs to be breached in order to allow the passage of movable operating parts, such as in the endoscope 1 according to the present invention the push-button 22 and the control button 6.

Accordingly, the present invention realises that by fitting a suitable cover 64 a sealed compartment for the main electronics may be provided within the handle, thus obviating the need for sealing the outer housing of the handle 2. The skilled person will understand that this applies, not only to the operating handle with a chassis 12 on which the preferred embodiments are based, but to operating handles for endoscopes in general. Thus the mounting plate 59 could also be mounted and directly within a shell part of an operating handle without a chassis 12, thereby protecting the main electronics, and possibly reinforcing the shell part mechanically.

The cover 64 has an edge 65 which essentially lies in a single plane except for a passage 66 for the cables 7, 63 to enter and exit the compartment. The edge 65 is thus adapted to engage a plane surface of the mounting plate 59 in close vicinity of the edge 68 of the mounting plate 59. As can be seen the edge 68 is preferably raised along the circumference of the mounting plate thus facilitating the positioning, attaching and sealing of the cover 64 with respect to the mounting plate 59. This attaching and sealing of the cover 64 with respect to the mounting plate 59 is preferably also performed using UV curable glue or resin, and accordingly the cover 64 is therefore also made of transparent plastic material, e.g. injection moulded like the chassis 12 and mounting plate 59. The chassis 12, mounting plate 59 and the cover 64 are preferably all made of the same material, thus facilitating the choice of a glue or resin with suitable adhesive and cohesive properties. This glue or resin may also be used to seal directly around the cable 7 and wires 63 at the passage 66. Preferably, the mounting plate 59 has a receptacle 69 in the shape of a half-pipe, serving to receive and hold the cable 7 and wires 63 as well as serve to limit the amount of UV curable glue or resin used when sealing the compartment around the cable 7 and wires 63.

In a preferred embodiment, however, the glue or resin does not seal directly around the cable 7 and wires 63. Instead the wires 63 are drawn from the compartment to the tip part 4 of the insertion tube 3 of the endoscope 1 within a wire or cable conduit 70, seen only in FIG. 1. Consequently, the sealing at the passage 66 will be around the conduit 70 and the cable 7. The conduit 70, in turn, is sealed at the tip part 4 at the distal end of the insertion tube 3 of the endoscope 1, thereby providing a sealed compartment extending all the way to the tip part 4, where it is preferably moulded in together with the camera housing. This sealed compartment protects the wires 63, which are relatively thin, against mechanical stress while preserving the sealing properties.

On the opposite side of the mounting plate 59 away from the compartment and the printed circuit board 62, two perpendicular flanges 77 are provided. These confer additional rigidity to the mounting plate 59 but their main purpose is to serve as protective barriers for a flexible hose 71 of a working channel of the endoscope 1. Like many prior art endoscopes, the endoscope 1 of the present invention comprises a working channel e.g. allowing liquid or fluid to be delivered to or extracted from the body cavity into which the endoscope has been advanced.

Starting from the distal end of the insertion tube 3 of the working channel as a first tube segment 72 attached to and preferably embedded in the tip part 4 at one end. The second end of the first tube segment 72 is connected to a first end of a second tube segment 73 by means of a short length of rigid tubing 74. Rigid in this sense is to mean more rigid than the second tube segment 73 which, in turn, is more rigid than the first tube segment 72 which has to comply with the flexibility requirements of the bending section 5. Similarly, the first tube segment 72 is more rigid than the flexible hose 71. In this respect it is preferred to make the flexible hose 71 of a first polyurethane elastomer and to make the first tube 72 of another polyurethane elastomer. Both polyurethane elastomers could be Pellethane®, which is available in different variants. The second tube segment 73 may also comprise polyurethane. The second end of the second tube segment 73 is connected to a T-joint 75 in connection with a connector 76 or lead-in mounted on chassis 12 in connection with a circular aperture 91 and serving to connect a hose of a suction or irrigation means to the working channel so as to extract or deliver aforesaid liquid or fluid to the body cavity into which the endoscope has been advanced.

However, in the endoscope 1 according to the present invention the working channel serves not only fluids or liquids, but also serves as a working channel for the tool 55, which means that a sealing is necessary where the motion of the lever arms 48 and 49 are transferred to the movable intermediate parts 53 and 54 which are largely accommodated within the first tube 72 and the second tube 73 of the working channel. This sealing is achieved by the use of the flexible hose 71 which is fixed at one end at the intermediate part 51 and at the other end at the T-shaped joint 75. The hose 71 may have a smooth surface in a relaxed state or it could be corrugated to form a bellows. The hose 71 is of a highly flexible thin-walled material as compared to the first tube 72 and the second tube 73 of the working channel, because it has to be able to comply with the relative motions between the intermediate parts 50, 51, 52 which is a compound translatory and rotational movement in two dimensions with respect to the chassis 12.

This compound translatory and rotational movement in two dimensions with respect to the chassis 12 make the hose 71 prone to damage from other movable parts of the endoscope 1. This is in particular the case for the cables 31 of the Bowden pulls 29 and certainly the crimps 33 even though some protection is achieved by guiding the cables 31 outside of the chassis 12 in the V-shaped grooves 40. As mentioned above, this protection is further increased by at least one of the flanges 77.

This compound translatory and rotational movement in two dimensions with respect to the chassis 12 is quite substantial, and to accommodate for the movement of the intermediate part 50 in one direction the rectangular aperture 36 is provided in the wall of the chassis 12. In the other direction the bottom 78 of the mounting plate between the flanges 77 serves as a strike plate to limit motion of the intermediate part 50 so as to be abutted by the claw like end 79 thereof which clamps and holds the intermediate member 52 inside the hose 71. This limitation of the motion prevents the section of the hose 71 located between the claw like end 79 and the intermediate part 51 to which the hose 71 is attached to be overstretched and rupture. The flanges 77 serve also to guide and control the movements of the hose 71 and claw like end 79, in particular in the lateral direction.

The entire insertion tube 3 is sealingly encapsulated in a flexible outer tube. The outer tube comprises a first outer tube section 80 and a second outer tube section 81 joined with a sleeve 82. Similarly to the working channel the first outer tube section 80 is more flexible than the second tube section 81 in order to comply with the movements of the bending section 5. The second tubular member 73 is however still quite flexible. More specifically, the second tubular member 73 and a second outer tube section 81 surrounding it are so flexible that they allow a loose knot to be tied on the insertion tube 3. The alternative is a rigid or semi-rigid endoscope where the insertion portion is rigid, only slightly bendable or hinged, and which does not allow a knot to be tied on the insertion tube. Preferably, the first outer tube section 80 is made from the very same material as the hose 71, either of them simply cut to a suitable length from a stock of tubular material for the respective purpose.

Returning now to FIG. 1a, a protective tubular member 90 can be seen. The intermediate part 11 has a slightly frustoconical section adapted to receive one end of the protective tubular member 90. The protective tubular member does not form part of the endoscope 1 as such but serves as a protective means during storage.

What is claimed is:
1. A video endoscope comprising:
    an operating handle;
    an insertion tube extending distally from the operating handle and having a distal end;
    a camera at the distal end of the insertion tube;
    a working channel extending from the operating handle to the distal end of the insertion tube; and
    control cables;
    the operating handle comprising:
        a housing, the working channel extending from the housing to the distal end of the insertion tube;

a control lever comprising a wall and trunnions extending laterally from the wall, the wall comprising a control lever immobilization aperture;

a first wall comprising a first support aperture and a first immobilization aperture;

a second wall comprising a second support aperture, the first support aperture and the second support aperture receiving the trunnions to facilitate rotation of the control lever, and the control lever immobilization aperture and the first immobilization aperture being alignable to receive a tool and thereby immobilize the control lever in a neutral position during attachment of the control cables to the control lever.

2. The video endoscope of claim 1, further comprising a T-joint with a connector mounted in the housing distally of the control lever.

3. The video endoscope of claim 2, wherein the T-joint comprises a portion of the working channel and the connector is adapted to establish fluid communication between a hose providing suction or irrigation and a distal end of the working channel through the T-joint.

4. The video endoscope of claim 3, further comprising a flexible hose forming part of the working channel and connected proximally of the T-joint, and an end connector sealing a proximal end of the hose.

5. The video endoscope of claim 4, further comprising a tool at the distal end of the insertion tube and a motion transfer linkage connecting the end connector with the tool within the working channel.

6. The video endoscope of claim 1, further comprising a chassis including the first wall and the second wall.

7. The video endoscope of claim 6, wherein the second wall comprises a second immobilization aperture.

8. The video endoscope of claim 7, further comprising a T-joint with a connector mounted in the housing distally of the control lever.

9. The video endoscope of claim 8, wherein the T-joint comprises a portion of the working channel and the connector is adapted to establish fluid communication between a hose providing suction or irrigation and a distal end of the working channel through the T-joint.

10. The video endoscope of claim 6, further comprising a tool at the distal end of the insertion tube, and a tool actuator having a depressed position, a released position, and an intermediate position intermediate the depressed position and the released position, wherein in the intermediate position the tool extends a maximum amount distally of the distal end of the insertion tube.

11. The video endoscope of claim 10, further comprising a motion transfer linkage within the working channel and connected to the tool, the motion transfer linkage extending the tool distally responsive to movement of the tool actuator from the released position to the intermediate position.

12. The video endoscope of claim 11, further comprising a mounting plate and a circuit board supported by the mounting plate, and perpendicular flanges extending from the mounting plate on a side opposite the circuit board, wherein the working channel extends between the perpendicular flanges.

13. The video endoscope of claim 1, wherein the insertion tube comprises a bending section and in the neutral position the bending section is unbent.

14. A method of assembly of a video endoscope, comprising:
providing a chassis including a first wall opposite a second wall, the first wall comprising a first support aperture and a first immobilization aperture, and the second wall comprising a second support aperture and second immobilization aperture;
providing a control lever comprising a wall and trunnions extending laterally from the wall, the wall comprising a control lever immobilization aperture;
supporting the trunnions with the first support aperture and the second support aperture;
aligning the first immobilization aperture, the second immobilization aperture and the control lever immobilization aperture;
placing a tool through the first immobilization aperture, the second immobilization aperture and the control lever immobilization aperture;
affixing a first control cable and a second control cable to the control lever; and
removing the tool.

15. The method of claim 14, further comprising:
securing the chassis to a portion of a housing;
securing an insertion tube to the portion of the housing;
after placing the tool and before removing the tool, pulling on a proximal end of each control cable until the insertion tube is in a neutral position; and
securing the proximal end of each control cable to the respective control cable.

16. The method of claim 15, wherein affixing the first control cable and the second control cable to the control lever comprises threading the proximal ends of the first control cable and the second control cable into respective pathways in the control lever.

17. The method of claim 16, wherein affixing the first control cable and the second control cable to the control lever further comprises crimping the proximal ends of the first control cable and the second control cable with, respectively, a first barrel and a second barrel.

* * * * *